United States Patent [19]

Bar-Or et al.

[11] Patent Number: 5,227,307
[45] Date of Patent: Jul. 13, 1993

US005227307A

[54] TEST FOR THE RAPID EVALUATION OF ISCHEMIC STATE

[75] Inventors: David Bar-Or, Englewood; Clive Solomons, Denver, both of Colo.

[73] Assignee: Diagnostic Markers, Inc., Englewood, Colo.

[21] Appl. No.: 736,583

[22] Filed: Jul. 26, 1991

[51] Int. Cl.$^5$ ............... G01N 33/00; G01N 21/00
[52] U.S. Cl. ............... 436/63; 436/74; 436/86; 436/87; 436/171; 435/16; 435/17; 435/26
[58] Field of Search ............ 436/86, 87, 171, 63, 436/74; 435/16, 17, 26

[56] References Cited

U.S. PATENT DOCUMENTS

| | | | |
|---|---|---|---|
| 3,955,926 | 5/1976 | Fischer | 436/92 |
| 4,379,848 | 4/1983 | Yeaw | 436/84 |
| 4,434,234 | 2/1984 | Adams et al. | 436/86 |
| 4,468,466 | 8/1984 | Morrissey | 436/86 |
| 4,486,282 | 12/1984 | Bier | 204/180 P |
| 4,492,753 | 1/1985 | Shell et al. | 435/17 |
| 4,713,327 | 12/1987 | Findlay et al. | 435/17 |
| 4,786,605 | 11/1988 | Mauck et al. | 436/86 |

OTHER PUBLICATIONS

Fleming, Nigel; et al. "A versatile transition metal salt reaction for a wide range of common biochemical reagents: an instantaneous and quantifiable color test". Anal. Biochem.; 154 (2), pp. 691-701, 1986.
*The New England Journal of Medicine*, (1991), 324, pp. 1417-1422, "The Role of Reperfusion-Induced Injury in the Pathogenesis of the . . . Odeh".
*J. Am Coll Cardio*, (1990), 16, pp. 1114-1119, "Plasma Homocyst(E)Ine Levels in Men With Premature Coronary Artery Disease", Genest et al.
"Superoxide Ion: Chemistry and Biological Implications", vol. II, *Oxygen Radicals in Biology*, Afanas'Ev.
*Glutathione*, "Interconversion of Glutathione and glutathione Disulfide" pp. 733-739.
*Quantitative Chemical Analysis*, pp. 199-203, "Reactions of the Cobaltous Ion, $CO++$", Vogel.
*Toxicity and Physiochemical Properties of Metals*, pp. 115-123, "Coordination and Chelation".
"Metal-Binding Groups of Proteins", Chapter IV, pp. 61-99.
*Metal Toxicity in Mammals*-2, pp. 282-289, "Chemical Toxicity of Metals and Metalloids", Venugopal et al.
*The New England Journal of Medicine*, (1990), 323, pp. 1781-1788, "Association of Perioperative Myocardial Ischemia with Cardiac Morbidity . . . ", Mangano et al.

*Primary Examiner*—Jill A. Johnston
*Assistant Examiner*—David Redding
*Attorney, Agent, or Firm*—Oblon, Spivak, McClelland, Maier & Neustadt

[57] ABSTRACT

A method for detecting ischemic states in a patient by contacting a sample of serum, plasma, fluid or tissue with a metal ion capable of binding to metal ion binding sites in the sample to form a mixture, and then detecting the presence of unbound metal ions to determine the occurrence of ischemia.

13 Claims, No Drawings

TEST FOR THE RAPID EVALUATION OF ISCHEMIC STATE

BACKGROUND OF THE INVENTION

1. Field of the Invention

The present invention relates to a rapid method for the detection of ischemic states and to a kit for use in such a method. More particularly, the invention relates to the measurement of protein bound thiol (SH) groups to determine the presence or absence of ischemia.

2. Discussion of the Background

Progressive coronary artery disease may be well advanced without significant clinical symptoms such as chest pain or dyspnea. The sudden occlusion of a branch of a coronary artery resulting in a myocardial infarction (MI) dramatically signals the presence of long standing arterial wall disease such as calcification of the intima and wall, as well as progressive stenosis of the lumen of the artery.

Immediately following an ischemic heart event, proteins are released into the blood. Well known proteins released after an ischemic heart event include creatine kinase (CK), serum glutamic oxalacetic transaminase (SGOT) and lactic dehydrogenase (LDH). One well known method of evaluating the occurrence of past ischemic heart events is the detection of these proteins in a patient's blood. U.S. Pat. No. 4,492,753 relates to a similar method of assessing the risk of future ischemic heart events. Injured heart tissue releases proteins to the bloodstream after both ischemic and non-ischemic events.

Patients undergoing non-cardiac surgery may experience perioperative ischemia. Electrocardiograms of these patients show ST-segment shifts with an ischemic cause which are highly correlated with the incidence of postoperative adverse cardiac events. However, ST-segment shifts also occur in the absence of ischemia and, therefore, this method does not distinguish ischemic from non-ischemic events.

Ischemia is frequently caused by arterial vessel disease. One feature of arterial vessel disease is the progression from the atheromatous state to the sclerotic state in which large quantities of calcium enter the arterial musculature. With the passage of time, arteriosclerosis progresses. The quantity of intracellular calcium increases while cardiac output remains essentially normal. The intracellular calcium activates the protease calpain which converts xanthine dehydrogenase to xanthine oxidase. Xanthine oxidase acts on xanthine and hypoxanthine to form free radicals, including the hydroxyl radical (OH.) and the superoxide radical ($O_2$.). These free radicals in turn oxidize cell membranes and proteins in the regions of the molecule which are rich in thiol groups. See "The Role of Perfusion—Induced Injury in the Pathogenesis of the Crush Syndrome", *New Engl. J. Med.*, 324:1417–1422 (1991).

A need exists for a method of distinguishing between ischemic and non-ischemic events, particularly in cardiac patients. After substantial research, the present method, based on metal-protein binding interactions, has been discovered which is capable of detecting ischemic states or events in a patient.

It is well known that metal ions are capable of binding to metal-binding groups in proteins ("Multiple Equilibria in Proteins", J. Steinhardt and J. Reynolds, Acad. Press, *CH-VI*, p 214 et seq.). Metal ions may form covalent linkages with proteins or, alternatively, form coordination complexes where the metal ion is chelated by ligands of the protein molecule (*Enzyme and Metabolic Inhibitors, Vol II.* J. L. Webb, (1966), Acad. Press, Chapt. 4, page 635 et seq.).

The ability of metal ions to bind proteins forms the basis of silver stains for proteins in polyacrylamide gels. U.S. Pat. No. 4,468,466 pretreats a gel with dithiothreitol (DTT) prior to staining with silver ions to reduce background staining. U.S. Pat. No. 4,434,234 provides a subsequent treatment with carbonate or sulfate salts to obtain different color stains.

In some instances, metal ions react with proteins to form precipitates. Metal-protein precipitation reactions have been used in methods for the quantitative determination of protein (U.S. Pat. No. 4,786,605) and in the total or fractional precipitation of proteins from a protein-containing solution (U.S. Pat. No. 4,486,282).

SUMMARY OF THE INVENTION

One object of the present invention is to provide a rapid method for detecting ischemic states in a patient.

A further object of the invention is to provide a method for evaluating rehabilitated patients suffering from ischemia (myocardial infarction) to determine circulatory effectiveness both at rest and during exercise.

Another object is to provide a rapid method for supplementing electrocardiographic results in determining the occurrence of true ischemic events.

A further object of the invention is to provide a kit for use with these methods.

These and other objects of the invention which will become apparent from the following specification have been achieved by the present method for detecting ischemia in a patient which comprises the steps of:

(a) contacting a serum, plasma, fluid or tissue sample of a patient with metal ions capable of binding to said sample at a metal ion-binding site, to form a mixture containing sample bound metal ions and non-sample bound metal ions, and (b) detecting the quantity of non-sample bound metal ions.

The invention also provides a kit capable of performing this method.

DETAILED DESCRIPTION OF THE PREFERRED EMBODIMENTS

The method of the present invention allows one to rapidly detect the presence of ischemic states in a patient. As used herein, the term "rapid" means that detection is possible within one hour, preferably within 30 minutes. As used herein, the term "ischemic event" means that the patient has experienced a local and temporary ischemia due to obstruction of the blood circulation to an organ.

The present invention provides a method for detecting ischemic states by a rapid process utilizing binding of metal ions to tissue proteins. In patients who have experienced an ischemic event, the number of thiol (SH) groups in the proteins contained in the serum, plasma, fluid or tissue of the patient is reduced due t oxidation by hydroxyl and superoxide radicals. This oxidation is believed to occur when intracellular calcium activates the protease calpain thereby forming xanthine oxidase from xanthine dehydrogenase. Xanthine oxidase acts on xanthine and hypoxanthine to yield free radicals which oxidize thiol groups in proteins. Oxidation of thiol groups results in the formation of more highly oxidized groups including disulfide (S—S), $SO_3$ etc. Applicants have discovered that the relative amount of protein bound SH groups in a sample functions as an indicator of oxidation occurring during the biological life of the protein. While not being bound by any particular theory, it is believed that the present method quantitates protein bound thiol groups in a sample as a measure of oxidative damage to the sample resulting from an ischemic event and thereby detects the ischemic event.

In the present method, a sample of serum, plasma, fluid or tissue from a patient is reacted with metal ions, generally in the form of an aqueous salt solution, so that the metal ions become bound to metal-binding sites on the protein contained in the sample. Metal ions bind to proteins containing metal ion-binding sites such as thiol, hydroxyl, carbonyl, amino, imidazole, hydroxymethionyl and guanidinium groups present on the amino acids which constitute the protein. The addition of the metal ions to the sample may precipitate a small amount of metal-protein complex, but such precipitation is not necessary nor detrimental to the process of the present invention.

A predetermined excess amount of metal ion salt is contacted with the protein in the sample and the metal ions are allowed to bind to the protein. By "excess" is meant an amount of metal ions greater than that which is stoichiometrically required to bind all available thiol groups in the protein of the sample. An excess of metal ions is added, so that the resulting mixture will contain free metal ions which may be detected to obtain a measure of the number of thiol groups present in the sample. Since the total amount of metal ions initially added is known, detection of the free metal ions remaining in the sample provides a measure of the amount of metal ions bound to the protein and therefore the amount of available thiol groups.

The free metal ions remaining after complexation of the protein thiol groups may be detected by any convenient means. Methods of detecting free metal ions in a sample are known in the art and include such methods as colorimetric reactions using a reagent which produces a colored substance upon reaction with the free metal ions, as well as direct measurement of the metal ions using methods including atomic absorption spectroscopy, atomic emission spectroscopy, etc. Any known method of detecting and quantitating metal ions in a sample may be used to detect the metal ions remaining after complexation with protein thiol groups. Preferably, the metal ions are detected colorimetrically by forming a colored complex and detecting the colored complex spectrophotometrically.

In a preferred embodiment of the colorimetric detection process, the metal salt/sample mixture is contacted with an aqueous solution of a thiol compound. The thiol compound reacts with the free metal ions to form a colored product. The intensity of the colored product is proportional to the quantity of metal ions present in the metal salt/sample mixture and therefore relates to the amount of protein bound thiol groups in the sample. By measuring the color intensity of the resulting colored solution, one is able to obtain a measure of the protein bound thiol groups originally present in the sample.

Obviously, color forming compounds other than thiol compounds may be used to form a colored product with the free metal ions, so long as a product having detectable color is formed when colorimetric detection is employed. Other suitable color-forming compounds include metal hydroxide solutions, ammonium hydroxide solutions, metal cyanide solutions, ammonium thiocyanate solutions, etc. These color-forming compounds and other compounds which form colored solutions with metal ions are well known in the art and described, for example, in A. I. Vogel, "Qualitative Chemical Analysis", Longmans, Green and Co., (1945); J. R. Marston and D. W. Dewey, *J. Exptl. Biol. Med. Sci.*, 18:343 1940); J. H. Yoe and C. J. Barton, *Ind. Enq. Chem., Anal. Ed.*, 12:405 (1940) and D. L. Tsalev and V. K. Zaprianov, "Spectroscopy", CRC Press, Boca Ratan FL (1983). These references are incorporated herein by reference for a more complete description of the reagents described therein which may be used as the color-forming compound in the present invention.

The sample which may be used in the present invention includes any tissue, serum, plasma or fluid sample containing proteins which are capable of binding metal ions. Tissue samples may be obtained from body organs to detect the occurrence of an ischemic event which affects the organ. Suitable organs include any organ having a blood supply or a protein matrix capable of oxidation, including the heart, kidney, intestine, arteries, veins, liver, etc. The sample may also be blood plasma and serum as well as other body fluids such as lymph, cerebrospinal fluid, saliva, etc. The sample may be obtained by well known conventional biopsy and fluid sampling techniques. Preferred samples are blood plasma and serum.

When colorimetric detection is used, the sample should not contain other metal binding compounds which bind or chelate the non-sample bound metal ions, thereby interfering with the colorimetric reaction. Metal binding compounds which should not be added to or present in the sample include citrate, oxalate, borate, ethylenediaminetetraacetic acid (EDTA), etc. used as anticoagulants, stabilizers or in buffer solutions.

Optimum results are obtained with samples containing a large concentration of proteins having thiol groups available for metal ion binding. Blood plasma and serum are preferred since these samples contain substantial amounts of albumin which has been found to be particularly effective for binding metal ions. Although blood plasma and serum are preferred samples, any sample containing a substantial concentration of proteins having available thiol groups may be used in the present invention.

Proteins which do not have available thiol groups for metal ion binding do not interfere with the present method. However, a sample containing only proteins which do not have available thiol groups will not be effective in binding metal ions and therefore ineffective in the present method. The presence or absence of thiol groups in a protein can be routinely assayed by known procedures. Proteins which may be present but do not sufficiently bind metal ions for use in the present method include hemoglobin, myoglobin, γ-globulin, transferrin, ferritin, glutathione (oxidized form) and putrescine. Similarly, the presence of other substances which do not bind metal ions do not interfere with the present method. Such non-interfering substances include lipoic acid, nitroglycerine, sodium nitrite, cystine, homocystine and homocysteine (in low concentrations as reported by Genest et. al.). The non-interference of homocysteine is surprising since homocysteine has an available thiol group and is known to be present in patients with premature artery disease (J. J. Genest et.

al., J. A. C. C., 1990, 16:1114–1119). Plasma levels of homocysteine on the order of 10 nanomolar per milliliter have been detected. However, this concentration is so low that it is incapable of measurably affecting metal ion binding. Therefore, these compounds do not interfere with the present method where they are present in free form or in protein-bound form.

The metal ions which may be reacted with the protein in the sample include any metal ion which is capable of binding to a metal ion-binding site on a protein. When colorimetric detection is used, the metal ion must also be capable of forming a colored product. Determination of metal ion binding to proteins and the formation of metal ion colored products is routine and easily accomplished using known methods. The formation of colored products is determined by preparing a dilution series of a desired color forming compound, for example, a thiol, in water and adding the chosen metal ion (as the metal salt) in serum o buffered solution. Color development is determined visually. The ability of a metal ion to bind with proteins in the sample may be determined by known means.

Metal ions are generally added to the sample as metal salts dissolved in an aqueous solution. Preferred metal ions are the transition metals of Groups $1b–7b$ and 8 of the Periodic Table of the Elements. Particularly preferred metal ions include V, As, Co, Sb, Cr, Mo, Mn, Ba, Zn, Ni, Hg, Cd, Fe, Pb, Au and Ag. Most preferred metal ions are Ni, Fe, Mn and Co. If desired, mixtures of these metal ions may be used.

The metal ions are preferably added to the sample as aqueous solutions. The solutions may be prepared by simply dissolving a metal ion salt in water to obtain the desired metal ion concentration. Any counter anion may be used for the metal ion so long as the counter ion does not interfere with metal ion-protein binding or the formation of the metal ion colored product when colorimetric detection means are used. Suitable anions include nitrate, nitrite, chloride, sulfate and carbonate. Cobalt chloride is particularly preferred.

Metal ion binding to proteins is pH dependent. The optimum pH for binding will vary with the individual metal ion used in the method. An appropriate pH for metal ion binding to the protein may be obtained by using a pH buffer to control the pH of the sample to the optimum pH rang for metal ion binding to the protein. For example, cobalt binding generally occurs over a pH range of 5–10.5, with a preferred binding range at pH 6.8–7.8, most preferably about 7.4. The use of cobalt is a preferred embodiment of the present invention since serum has sufficient buffering power over the narrow preferred pH binding range of cobalt (6.8–7.8) such that additional buffering is unnecessary. However, if sample and metal ions are used which require buffering, a buffer may be added to the sample to adjust the pH to the desired optimum binding range. Such buffers are well known and commercially available.

Metal ion-protein binding is not substantially temperature sensitive. The present process may be conducted at temperatures ranging from room temperature (20° C.) up to and above 50° C. Preferably, the method is conducted at about 20°–25° C. If sample has been chilled or frozen, the sample is allowed to thaw to ambient temperature prior to testing.

When directly detecting the free metal ions using a method such as atomic absorption spectroscopy, a sample suitable for analysis may be prepared directly from the sample. When using such methods, it is preferable to add the metal ions to the sample in the form of an aqueous solution which, after binding of the metal to the protein thiol groups, provides a sample solution containing unbound metal ions. Additional sample preparation steps such as filtration, for example, may be performed to remove any residual precipitates.

The direct detection method (atomic absorption spectroscopy) allows one to qualitatively and quantitatively determine the presence and amount of free metal ions present. If the initial amount of metal ions in the aqueous solution is known, detection of the free metal ions present in the solution after protein binding provides a measurement of the number of free protein thiol groups and hence a measurement of thiol group oxidation. It is expedient to use standardized metal ion solutions containing a known quantity of metal ions. This enables routine analysis of samples in a medical laboratory, for example.

The quantity of free metal ions in the sample may also be detected by colorimetric means. After the sample has been contacted with metal ions, the mixture is contacted with an aqueous solution of color forming compound (thiol) which reacts with any unbound metal ions. The color forming compound should be soluble in water at a sufficient concentration to react with all available unbound metal ions. Additionally, the color forming compound should not absorb light in the absence of metal ions in the wavelength range at which the colored metal ion product is detected. Generally, it is desirable that the free color forming compound not absorb light in the absence of metal ions in the detection wavelength range of about 400–900 nm. The color forming compound should also be stable to any degradation by biological components present in the sample and should be stable at the pH and temperature conditions of the method.

Although any color forming compound having the properties noted above may be used in the present method, thiols are preferred and include $C_{2-6}$ alkyl thioalcohols such as mercaptoethanol, 2,3-dimercaptopropanol, dithioerythritol and dithiothreitol; $C_{2-6}$ alkyl thioamines, such as mercaptoethylamine, mercaptopropylamine, etc.; $C_{2-10}$ alkyl thiomonocarboxylic acids and diacids, such as dimercaptosuccinic acid, mercaptopropionic acid, mercaptoacetic acid and mercaptomalonic acid; di-$C_{1-6}$ alkyldithiocarbamic acids such as dimethyldithiocarbamic acid, diethyldithiocarbamic acid, etc.; thiol-containing amino acids and peptides such as cysteine, $\beta$-mercaptoisoleucine, glutathione, etc.; and thiol-containing enzymes such as papain, phosphoenol pyruvate, carboxykinase, 3-phosphoglyceraldehyde dehydrogenase, propionyl coenzyme A carboxylase, streptococcal protease and thiol-containing carboxypeptidases. Other suitable thiols include 1,3,4-thiadiazole-2,5-dithiol, coenzyme-A 4'-phosphopantetheine and penicillamine.

Other color forming compounds which may be used include pyridine-2-azo-paradimethyl-aniline, $\alpha$-nitroso-B-naphthol, $\beta$-nitroso-$\alpha$-naphthol, dithiooxamide, thiosemicarbazide, $C_{1-6}$ alkyl thiosemicarbazides such as 2-methyl-3-thiosemicarbazide, 4-methyl-3-thiosemicarbazide and 4-ethyl-3-thiosemicarbazide, formaldehyde-tryptophan, salicylaldehyde, quinoxaline-2-carbosaldehyde-2-chloroacetyl-aminomethyl-benzimidazole and proflavine salts such as proflavine hemisulfate and hydrochloride.

Particularly preferred compounds are dithiothreitol, cysteine and glutathione.

The color forming compound may be prepared as an aqueous solution having a concentration sufficient to react with all available unbound metal ions. If the concentration of the color forming compound is too high, a large amount of precipitate with the metal ions may form. If the solution is too dilute, detection of the colored product is difficult. In practice, the concentration of the solution is adjusted so as to provide a sufficiently colored solution so that absorption of light can be detected using a spectrophotometer or similar detection equipment. Optimization of the concentration of the color forming compound can be routinely determined.

The amount of metal ion added to the sample must be sufficient to bind all available protein bound thiol groups and provide an excess of detectable metal ions.

When colorimetric detection is used, the amount of metal ions added should be sufficient to provide a colored product which can be detected by a detector such as a spectrophotometer. The concentration of the metal ion solution is preferably about 0.001-0.100M, more preferably 0.002-0.010M. The amount of metal ions added to the sample will vary and may be routinely adjusted so long as the unbound metal ions form sufficient colored product to be reliably detected. If too much metal ion is added, the resulting color intensity is too high to be accurately determined by the detector. If the amount of metal ion is too low (the amount of serum is too high) long equilibration periods are necessary and the color yield is too small. The relative amounts of these reactants may be routinely determined to provide optimum absorbance readings with a spectrophotometer or other detector.

If necessary, a salt solution isosmotic with blood may be added to the sample after addition of thiol reagent to provide a dilute solution having a color intensity suitable for detection. Dilution with isosmotic solutions minimizes protein precipitation and turbidity. Preferred isosmotic solutions are solutions prepared from sodium chloride, although other salts such as potassium chloride and lithium chloride are also suitable. If the addition of thiol solution provides an adequate color intensity for detection, additional dilution with the isosmotic solution is not necessary.

After addition of the color forming compound solution to the metal ion-protein mixture and subsequent dilution, if necessary, the color intensity of the resulting product may be measured with a conventional spectrophotometer. The absorbance of the colored product is generally measured at the maximum absorbance wavelength for the colored product which is produced. Obviously, the colored product will depend upon the particular color forming compound and metal ion which are used in the method. The optimum absorbance wavelength can be routinely determined by known procedures.

The present invention also provides a kit for use in performing the above-described method. The test kit of the present invention contains a metal salt, a color forming compound and, if necessary, a solution isosmotic with blood plasma or serum. Aqueous solutions of the metal salt and color forming compound may be formed by simply adding water to the compounds contained in the test kit to obtain the desired solutions. Alternatively, the kit may contain aqueous solutions of the metal salt and color forming compound directly. The kit may also contain a test vessel for mixing the test sample with the three components noted above. Rapid detection of ischemic states is possible by mixing a sample with the solution of metal salt, and detecting the amount of free metal ions.

Samples taken from normal patients who have not experienced an ischemic event produce sample solutions having a low concentration of detectable metal ions and a lower absorbance (less color intensity) than samples taken from patients who have experienced an ischemic event. Samples taken from patients who have experienced non-cardiogenic chest pain, for example, contain substantially fewer detectable metal ions than patients who have experienced an ischemic event such as myocardial infarction or unstable angina. The present method allows one to test samples from a patient complaining of chest pain and rapidly determine whether this chest pain is associated with an ischemic event or is simply non-cardiogenic chest pain. Similarly, the progress of a patient recovering from an ischemic episode such as myocardial infarction may be evaluated by sampling patient tissue at regular intervals to evaluate circulatory effectiveness and the abatement of ischemic conditions.

Other features of the invention will become apparent in the course of the following descriptions of exemplary embodiments which are given for illustration of the invention and are not intended to be limiting thereof.

EXAMPLES

In a preferred embodiment, cobalt was selected to react with protein bound thiol groups. Unreacted cobalt was detected with dithiothreitol which forms a brown-colored product with cobalt ions. The brown-colored product was detected using a spectrophotometer at a wavelength of 470 nm.

EXAMPLE 1

Materials

Cobalt Solution: 200 mg $CoCl_2.6H_2O$ was dissolved in 2 ml of distilled water. For use, this solution was diluted 100 fold.

Dithiothreitol Solution: 15 mg of dithiothreitol was dissolved in 10 ml distilled water.

Saline Solution: 0.9 g of sodium chloride was dissolved in 100 ml water.

Serum: 2-10 ml of blood was obtained by peripheral venipuncture and allowed to clot. The tube was centrifuged at 3,000 rpm for 5 minutes and the supernatant serum transferred to a separate glass or plastic container.

Plasma: 2-10 ml of blood was drawn into a heparinized vacutainer. The tube was centrifuged at 3,000 rpm for 5 minutes and the supernatant plasma transferred to a separate glass or plastic container.

Sera were obtained from 22 patients known to have had a myocardial infarction or ischemic episode. To 0.2 ml serum or plasma from each of these patients, in a test tube or cuvette, was added 50 $\mu$l of $CoCl_2.6H_2O$ and the mixture was allowed to stand for 10 minutes. 50 $\mu$l of dithiothreitol solution was added to each tube followed by mixing. The tubes were then allowed to stand at room temperature for 2 minutes to allow formation of the colored product. 1 ml of 0.9 % wt/vol NaCl was then added to each tube followed by mixing and the absorbance of each tube was read using a spectrophotometer at 470 nm. Control tubes were prepared and tested by adding identical serum, cobalt chloride solution and sodium chloride solution but no dithiothreitol solution. The absorbance of the control tubes was also read at 470 nm and substracted from the test result.

The 22 patients known to have a myocardial infarction or an ischemic episode were found to have a mean value and standard deviation of 0.62±0.15 (n=22). Controls had a mean and standard deviation of 0.27±0.05 (n=11). The means were statistically significant by the student's t-test. Normal patients with non-cardiogenic chest pain had a mean value of 0.32 ±0.05 (n=15). Patients with unstable angina had a mean value of 0.61±0.22 (n=8). See Table 1.

TABLE 1

| Absorbance | Myocardial Infarction (%) | Unstable Angina (%) | Non-Cardiogenic Chest Pain (%) | Normal (%) |
| --- | --- | --- | --- | --- |
| 0.2-0.29 | — | — | 20.0 | 72.8 |
| 0.3-0.39 | 4.5 | 12.5 | 80.0 | 27.3 |
| 0.4-0.49 | 18.0 | 12.5 | — | — |
| 0.5-0.59 | 22.6 | 37.5 | — | — |
| 0.6-0.69 | 18.1 | 12.5 | — | — |
| 0.7-0.79 | 18.0 | — | — | — |
| 0.8-0.89 | 18.0 | — | — | — |
| 0.9-0.99 | — | 25.0 | — | — |
| $X^- \pm S.D.^*$ | 0.62 ± 0.15 | 0.61 ± 0.22 | 0.32 ± 0.047 | 0.27 ± 0.048 |
| t = 6.9 p < 0.0001 | + | — | + | — |
| t = 9.3 p < 0.0001 | + | — | — | + |
| t = 0.13 p < 0.5 | + | + | — | — |

*S.D. = Standard Deduction

These results indicate that the present method can be used to detect ischemic states. The present method is effective in distinguishing between ischemic cardiogenic chest pain and non-cardiogenic chest pain.

Obviously, numerous modifications and variations of the present invention are possible in light of the above teachings. It is therefore to be understood that within the scope of the appended claims, the invention may be practiced other than as specifically described herein.

What is new and desired to be secured by Letters Patent of the United States is:

1. A method of detecting the occurrence or non-occurrence of an ischemic event in a patient, comprising the steps of:
   (a) contacting a serum, plasma, fluid or tissue sample of said patient with metal ions capable of binding to thiol groups in said sample, to form a mixture containing sample bound metal ions and non-sample bound metal ions,
   (b) directly detecting the amount of non-sample bound metal ions by atomic absorption or atomic emission spectroscopy to determine the amount of said thiol groups in the sample, and
   (c) correlating the amount of thiol groups in the sample to determine the occurrence or non-occurrence of an ischemic event.

2. The method of claim 1, wherein said sample is serum or plasma.

3. The method of claim 1, wherein said metal ion is a transition metal ion of Groups 1b–7b or 8 of the Periodic Table of the elements.

4. The method of claim 1, wherein said metal ion is selected from the group consisting of V, As, Co, Sb, Cr, Mo, Mn, Ba, Zn, Ni, Hg, Cd, Fe, Pb, Au and Ag.

5. The method of claim 1, wherein said metal ion is cobalt.

6. A method of detecting the occurrence or non-occurrence of an ischematic event in a patient, comprising the steps of:
   (a) contacting a serum, plasma, fluid or tissue sample of said patient with metal ions capable of binding to thiol groups in said sample, said metal ions being selected from the groups consisting of V, As, Co, Sb, Cr, Mo, Mn, Ba, Zn, Ni, Hg, Cd, Fe, Pb, Au and Ag, to form a mixture containing sample bound metal ions and non-sample bound metal ions.
   (b) contacting said mixture with an aqueous color forming compound solution to form a colored solution,
   (c) determining the color intensity of said colored solution to detect the presence of non-sample bound metal ions and detect the amount of said thiol groups in the sample, and
   (d) correlating the amount of thiol groups in the sample to determine the occurrence or non-occurrence of an ischemic event,
   wherein said color forming compound is a $C_{2-6}$ alkyl thioalcohol, $C_{2-6}$ alkyl thioamine, $C_{2-10}$ alkyl thiomonocarboxylic acid, $C_{2-10}$ alkyl thiodicarboxylic acid, $C_{2-10}$ alkyl dithiodicarboxylic acid, di-$Ch_{1-6}$ alkyl dithiocarbamic acid, thiol-containing amino acid, thiol-containing peptide, thiol-containing enzyme, metal hydroxide ammonium hydroxide, metal cyanide or ammonium thiocyanate.

7. The method of claim 6, further comprising diluting said colored solution with an aqueous solution isosmotic with blood serum or plasma prior to said detecting step.

8. The method of claim 6, wherein said color forming compound is selected from the group consisting of dithiothreitol, cysteine or glutathione.

9. The method of claim 8, wherein said color forming compound is dithiothreitol.

10. The method of claim 6, wherein said detecting step is conducted in a pH range of 5–10.5.

11. The method of claim 6, wherein said detecting step is conducted using a spectrophotometer.

12. The method of claim 6, wherein said sample is serum of plasma.

13. The method of claim 6, wherein said metal ion is cobalt.

* * * * *